United States Patent [19]
Bullock

[11] 4,246,907
[45] Jan. 27, 1981

[54] METHOD FOR IDENTIFYING AN OVULATION PHASE WITHIN A MENSTRUAL CYCLE OF A WOMAN

[76] Inventor: Russel F. Bullock, 4401 Parkchester Cir., Las Vegas, Nev. 89108

[21] Appl. No.: 7,383

[22] Filed: Jan. 29, 1979

[51] Int. Cl.³ ............................................. A61B 5/04
[52] U.S. Cl. ................................................. 128/738
[58] Field of Search ............................... 128/738, 734

[56] References Cited

U.S. PATENT DOCUMENTS

| | | | |
|---|---|---|---|
| 3,064,641 | 11/1962 | Manenti et al. | 128/734 |
| 3,920,003 | 11/1975 | Ash et al. | 128/738 X |
| 3,924,609 | 12/1975 | Friedenberg et al. | 128/738 |
| 4,148,304 | 4/1979 | Mull | 128/738 |

FOREIGN PATENT DOCUMENTS 2655716  6/1978  Fed. Rep. of Germany ........... 128/738

*Primary Examiner*—Kyle L. Howell
*Attorney, Agent, or Firm*—Jackson, Jones & Price

[57] ABSTRACT

At least the polarity of a potential difference between two spaced apart portions of the body of a woman is repeatedly measured on each day throughout at least a substantial portion of the days of a menstrual cycle of the woman. The days in which the measurements indicate at least two readings of oppposite polarity are identified as days immediately preceding the time of ovulation of the woman.

17 Claims, 7 Drawing Figures

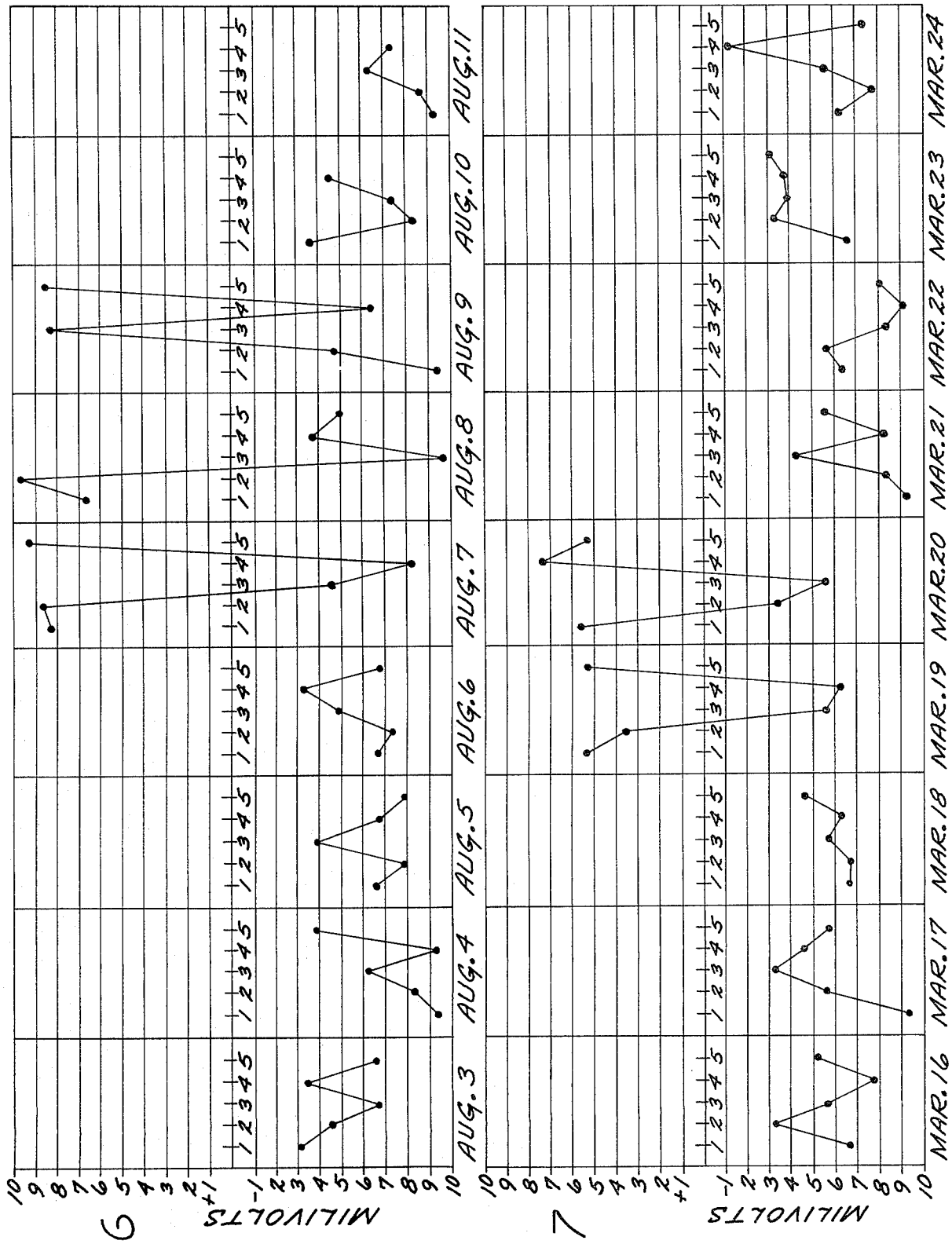

METHOD FOR IDENTIFYING AN OVULATION PHASE WITHIN A MENSTRUAL CYCLE OF A WOMAN

BACKGROUND OF THE INVENTION

1. Field of the Invention

The present invention relates to a process of identifying an ovulation phase within the menstrual cycle of a woman, and more particularly to a process of measuring several times in direct succession a direct current potential between two spaced apart portions of the body of the woman and evaluating the measurements to identify the ovulation phase.

2. Description of the Prior Art

Medical experiments wherein direct current potentials between two spaced apart portions of the human body were measured, date back more than 30 years from the present.

Early medical researchers have proven conclusively that direct current potential or voltage differences of approximately 1-100 milivolts magnitude may exist between different portions of the human body. Efforts were made in the prior art to find a correlation between variations and time dependent fluctuations of these voltage differences and changes in the physiological state of human beings.

The different nature of experiments measuring skin resistance as in the use of polygraph type devices, and measuring potential differences between different points of the human body was recognized early in the prior art.

An article authored by H. S. Burr et al titled "Bio-Electric Correlates of Human Ovulation" appeared in the Yale Journal of Biology and Medicine Vol. 10 pages 155–160 (1937). This article described an experiment wherein the potential or voltage difference between the symphysis pubis and the vagina of a healthy adult woman was monitored for 4 days preceding ovulation. The experiment showed that prior to ovulation the potential of the vagina has shifted from a negative to a positive value. The authors suggested that a technique of monitoring the above described potential difference makes a determination of the time of ovulation possible.

In an article authored by Louis Langman et al titled "A Technique to Aid in the Detection of Malignancy of the Female Genital Tract", American Journal of Obstetrics and Gynecology, St. Louis, Volume 57, pages 274–281, 1949, the authors described experiments aimed at determining or predicting malignancy in the female genital tract. Potential or voltage differences between the cervix and the ventral abdominal wall were measured. The authors found, among other things, that in healthy patients a negative potential of the genital tract could be correlated with ovulation.

U.S. Pat. No. 3,920,003 describes an apparatus for detecting small electrical potential differences between the vagina and another location of the body. One of the asserted uses of the apparatus is the detection of ovulation. The patent disclosure states that the potential of the vagina is negative with respect to other parts of the body, but this potential may fall to zero or reverse in sign when ovulation occurs. The patent suggests the monitoring of the potentials between the vagina and other points of the body for the purpose of detection of ovulation.

U.S. Pat. No. 3,924,609 describes an apparatus and a method for detecting the phase of ovulation in a mammalian female, including the human female. The method employs a voltmeter whose electrodes are brought into contact with fingers of each hand of the woman. This disclosure teaches that prior to ovulation the measured potential from a negative value normally rises towards and even above zero, and reaches a peak at the time of ovulation. A potential-versus-time graph as depicted in this prior art patent is substantially reproduced in the present application as FIG. 3 for the sake of graphically showing the state of the prior art.

In attempting to measure potential differences of 1–100 milivolt magnitude between various points of the human body, great care must be taken. A voltage meter having a very high impedance and of at least 10 megaohms which draws practically no current, must be utilized. Furthermore contaminating contact potentials which may arise on contact of an electrode with the skin must be avoided or compensated for. The prior art has generally recognized this. The above cited article in the Yale Journal of Biology and Medicine describes the use of silver—silver chloride electrodes as skin contacts. More specifically, silver electrodes which were coated with silver chloride were brought into contact with the human skin through the intermediacy of a saline solution bridge.

An electrical circuit which is suitable for measuring low voltages associated with the human body is described e.g. in U.S. Pat. Nos. 3,924,609 and 3,920,003. Recent advances in microprocessor or "chip" technology as well as advances in the flat panel information display technology have made possible corresponding advances in volt meter design technology.

Although, as it was described above, the prior art suggested various methods for the detection of the ovulation phase of the human menstrual cycle, the prior art methods have not gained widespread acceptance. The reliability of the prior methods has not been adequately proven. Furthermore, the inconvenience associated with some of the prior art methods, such as insertion of an electrode into the vagina, has understandably discouraged the widespread use of these methods. Many healthy women merely seek an aid in family planning through the accurate detection of their ovulation cycle and are reluctant to use inconvenient methods. Accordingly, there is room in the art for the improved ovulation detection method of the present invention.

SUMMARY OF THE INVENTION

It is an object of the present invention to provide a method whereby the menstrual cycle of a woman can be monitored and a phase preparatory to ovulation can be detected.

It is another object of the present invention to provide an improved method for monitoring the menstrual cycle of a woman which can be readily performed by the woman without constant medical supervision.

It is still a further object of the present invention to provide an improved method for monitoring the menstrual cycle of a woman which enables family planning with satisfactory accuracy and without undue inconvenience to the woman.

These and other objects and advantages are attained by a process wherein a pair of suitable electrodes representing the probes of a suitably sensitive voltmeter are applied to two spaced apart points on the skin of a woman's body. At least the polarity of a voltage or potential difference between the two spaced apart points is measured. The measurement is repeated on the same day a plurality of times. The above described series of measurements is performed each day throughout at least a substantial portion of the days of the menstrual cycle of the woman. Those days in which the measurements show readings including at least two readings of opposite polarity are selected and identified as days immediately preceding a time of ovulation within the menstrual cycle.

The objects and features of the present invention are set forth in the appended claims. The present invention may be best understood by reference to the following description, taken in connection with the accompanying drawings in which like numerals indicate like parts.

BRIEF DESCRIPTION OF THE DRAWINGS

FIG. 6 is a graph wherein for several selected days of the graph of FIG. 4 the measured potential differences are plotted against time, with approximately 5 minutes or less time elapsing between the respective points 1, 2, 3, etc. indicated on the abscissa; and FIG. 7 is a graph of the same nature as the graph of FIG. 6 representing several selected days of the graph of FIG. 5.

DESCRIPTION OF THE PREFERRED EMBODIMENT

The following specification taken in conjunction with the drawings sets forth the preferred embodiment of the present invention. The embodiment of the invention disclosed herein is the best mode contemplated by the inventor for carrying out his invention in a commercial environment, although it should be understood that various modifications can be accomplished within the parameters of the present invention.

Figure 1:
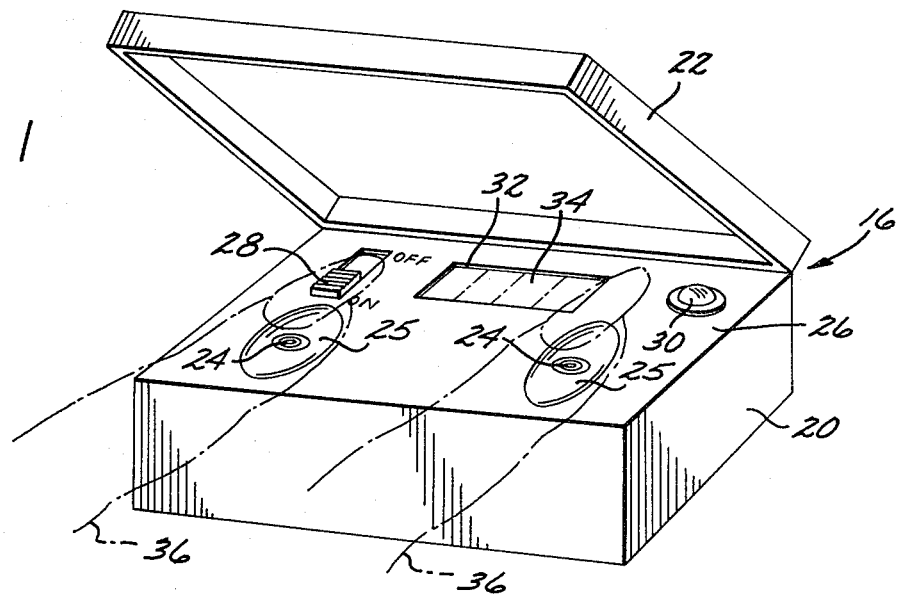
FIG. 1 is a perspective view of a step of the process of present invention wherein an index finger, shown by phantom lines, of each hand of a woman is being applied to electrodes of a sensitive voltage meter.

Referring now to the perspective view of FIG. 1, a step of the process of the present invention and a voltage meter 16 particularly adapted for carrying out the process is disclosed.

Figure 2:
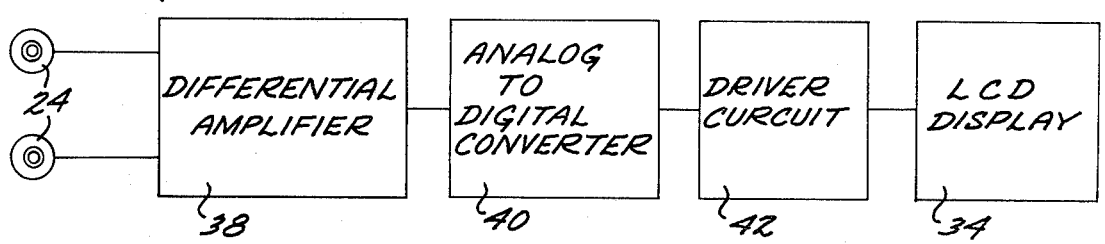
FIG. 2 is a block diagrammatic representation of a circuit and of a liquid crystal digital display of the voltage meter.

A suitable circuit 18, schematically shown in FIG. 2, for the voltage meter 16 is mounted in a box shaped base 20 which is covered by a hinged lid 22. Two spaced apart electrodes 24 are located in oval shaped depressions on an upper surface 26 of the base 20. An on-and-off switch 28, and an indicator light 30 which glows when a battery (not shown) located inside the base 20, is weak, are likewise located on the upper surface 26. A window 32 incorporating a liquid crystal type digital display 34 is disposed on the upper surface 26 of the base 20.

The electrodes 24 and the electrical circuit 18 are particularly adapted for measuring potential differences in the 1-100 milivolt range which may exist between two points of a human body. Although the present state of the electronic arts readily permits the design of such circuit the nature of the circuit 18 and of the electrodes 24 is briefly described here to the extent deemed necessary to permit a full understanding of the present invention.

The electrodes 24, each of which comes into contact with the index finger 36 of one hand of a woman (not shown), are designed to avoid the creation of undesirable contact potentials between the finger 36 and the electrode 24. As the prior art has discovered it, silver electrodes coated with a layer of silver chloride are eminently suited for this purpose. Therefore, the electrodes 24 of the voltage meter 16 comprise such silver chloride coated silver electrodes.

In order to assure good electrical contact between the electrodes 24 and the fingers 36 it may be desirable to apply a small amount of suitable electrolyte paste on the finger 36 in the area on which contact with the electrodes 24 is to be made. An electrolyte paste suitable for such application may comprise a mixture of 0.9% by weight saline solution with the commercially available electrode paste product of Park-Davis Co. sold under the tradename Unibase.

As this is well known in the art, a circuit adapted for measuring very small voltage differences must draw virtually no current. The circuit 18 incorporated in the voltage meter meets this test. The electrical circuit, as it is schematically shown in FIG. 2 includes a differential amplifier 38, an analog-to-digital converter 40 and a driver circuit 42 to drive the 3 digit liquid crystal display 34.

Employing the digital display 34 facilitates the observation of the measured voltage differences. This is particularly true because many of the women who may utilize the voltage meter 16 described here are unfamiliar with the technique of reading conventional, analog, d'Arsonval type voltmeters.

The circuit 18 by means of its liquid crystal display 34 is designed to display the positive or negative sign of the voltages measured in addition to their numerical value. As is further explained below, observing the sign of the measured voltage differences has great importance in the practice of the process of the present invention. Furthermore, it will become apparent from the description below that the process of the present invention may also be practiced by the use of a voltage meter and display which merely indicates the sign of the voltage differences. Nevertheless, the preferred embodiment of the process described here utilizes a voltage meter which is capable of displaying actual values of the measured voltages.

Certain optional features added to the circuit 18 described above, are desirable in the practice of the process of the present invention. Such a desirable feature is a circuit (not shown) which indicates a weak state of the battery (not shown) through the indicator light 30. If desired, a suitable circuit may be provided for returning the voltmeter reading to zero in the absence of any potential being applied across the electrodes 24. Such a circuit may include an adjustable potentiometer for permitting the meters reading to be manually adjusted to zero or other means capable of automatically zeroing the meter reading. It will be readily apparent to those skilled in the electronic arts that additional modifications may be made in the voltage meter 16.

Referring again to the perspective view of FIG. 1, a step of the process of the present invention is shown. In this step a woman applies one of the fingers of each hand, preferably the index fingers 36, to each of the electrodes 24 of the voltage meter 16. The fingers 36 are moistened with the electrolyte paste (not shown). Experiments have shown that immediately after the application of the fingers 36 to the electrodes 24 the voltage meter may exhibit erratic, unstabilized voltage read-outs for a short while. The voltage read-out, however, stabilizes rapidly, and a relatively constant reading on the display 34 is noted.

The stabilized voltage reading which reflects the potential difference between the two fingers 36 is recorded by writing or otherwise. The woman then reapplies her fingers 36 to the electrodes 24 and the formerly described steps of obtaining a relatively stable read-out of the voltage difference and recordation of the same, are repeated.

Prior to reapplying the fingers 36 to the electrodes 24 it may be preferrable to clean the fingers 36 from used electrolyte paste and apply fresh paste. The steps of applying the fingers and measuring the voltage difference between them is repeated several times, preferably 4 or 5 times. The time intervals occurring between each measurement usually comprise approximately one minute. This is however subject to variations according to individual preferences and habits of the woman who is conducting the measurements. Nevertheless, the entire process of measuring 5 stable readings can be completed in approximately ½ an hour, and usually in much less time.

The series of measurements described above are repeated preferrably every day throughout the entire menstrual cycle of the woman. Rigorous adherence to the requirement of taking measurements every day throughout the entire menstrual cycle, except during the period of menstruation, is highly preferred. Nevertheless, it is recognized that due to various reasons a woman practicing the process of the present invention may occasionally skip a day, or may not perform the measurements throughout the entire time period of her menstrual cycle. In such a case satisfactory results may still be obtained unless, through inadvertence, the days immediately preceding ovulation are skipped.

Figure 3:
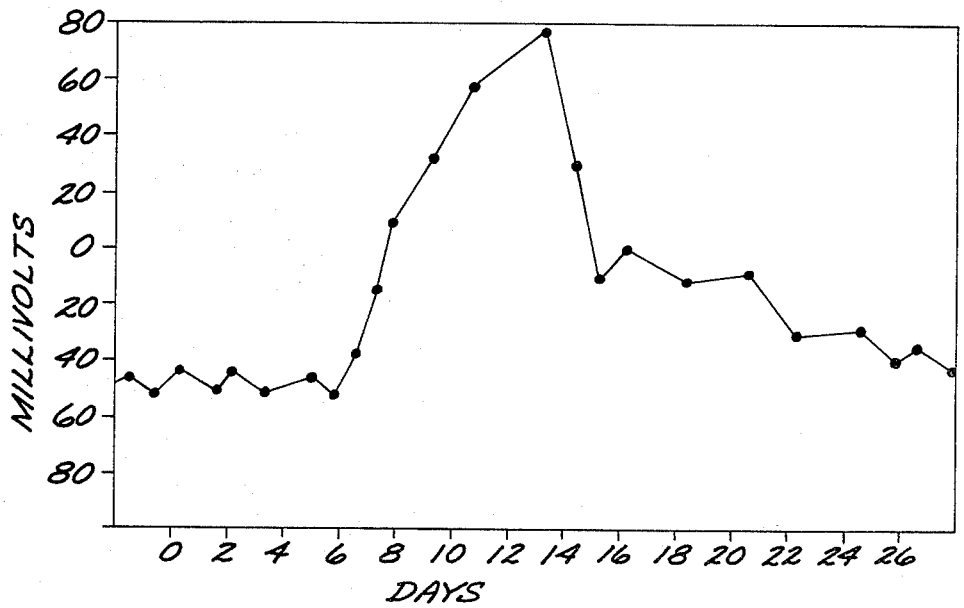
FIG. 3 is a graph obtained in the prior art, wherein potential differences expressed in milivolts obtained daily between two spaced apart points on a woman's body are plotted against successive days of the menstrual cycle.

Referring now to the graph of FIG. 3 a voltage-versus-day curve, obtained in the prior art is presented reflecting the results of daily measurements. The time of ovulation is suggested by the prior art to be the time of peak voltage as indicated on the graph. The prior art further suggested that ovulation can be predicted from the slope of the rising curve prior to ovulation.

Figure 4:
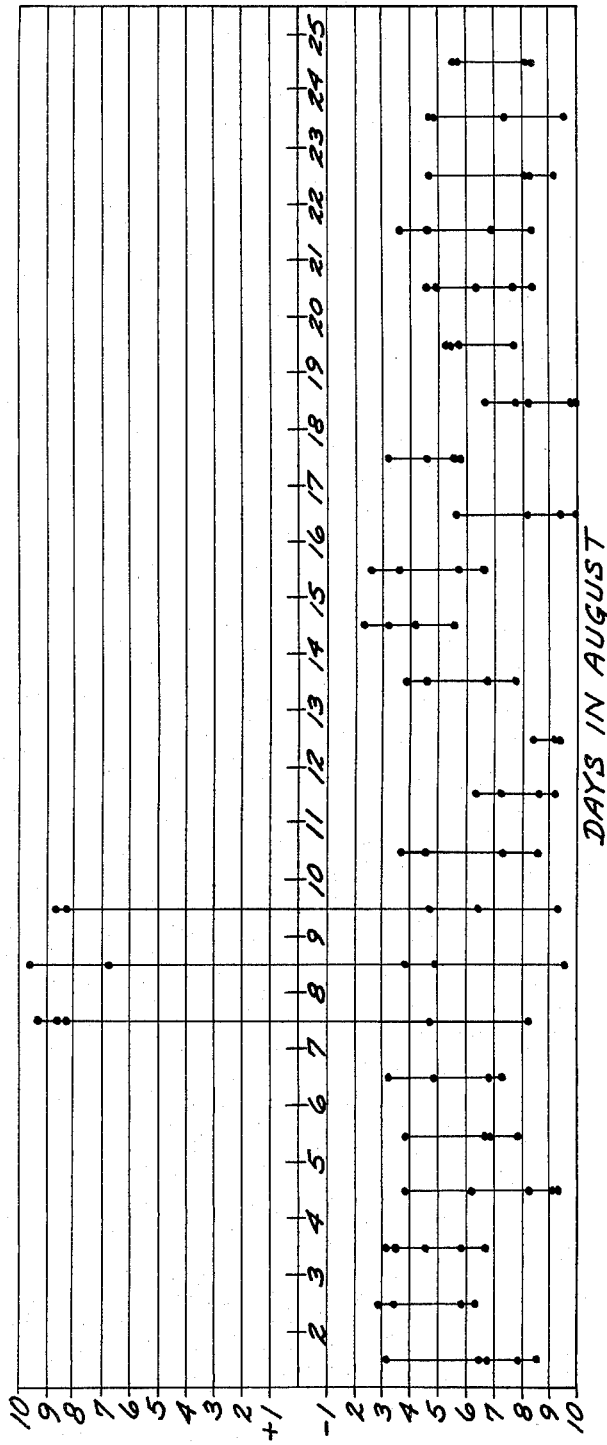
FIG. 4 is a graph showing actual test results of the method of the present invention, wherein a plurality of voltage measurements taken each day are plotted against successive days of the menstrual cycle.
Figure 5:
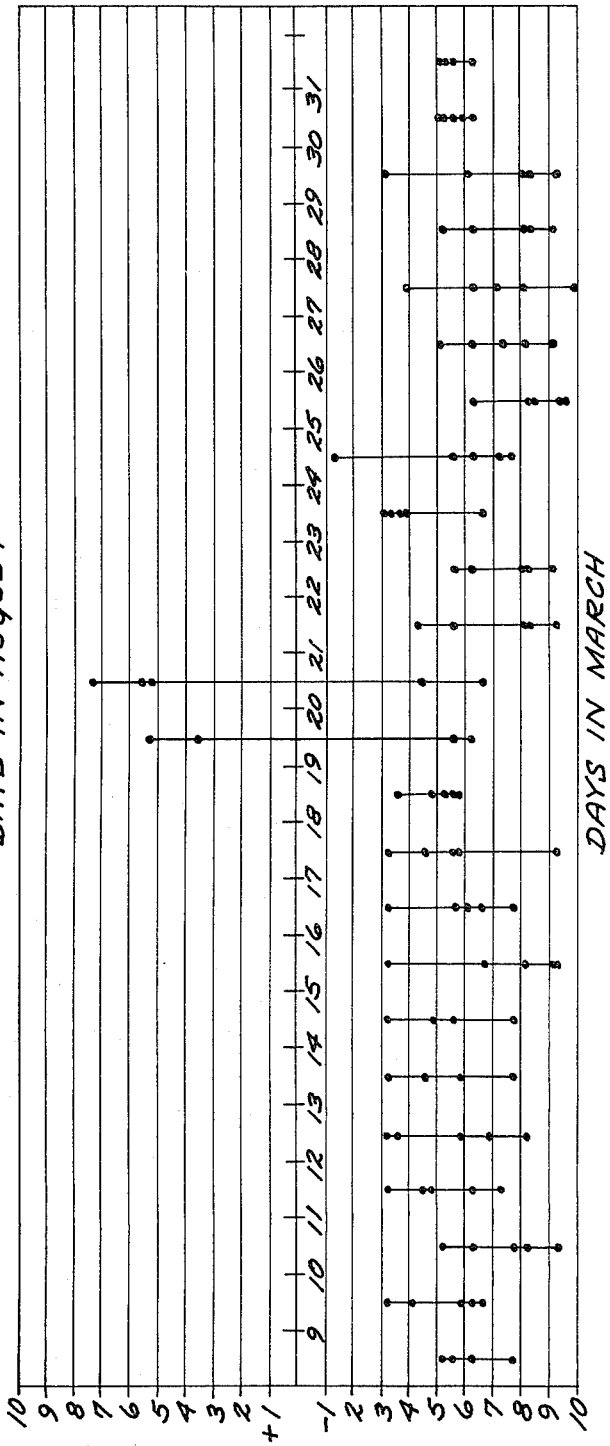
FIG. 5 is another graph of the same nature as the graph of FIG. 4 representing another actual test.

Having examined the prior art curve of FIG. 3, reference is made to FIGS. 4 and 5 wherein typical test results of the present invention are illustrated.

The points connected by a vertical line on these graphs show the measured potential differences on a given day. The graphs show such measurements throughout a substantial portion of the days of the menstrual cycles of the particular subject test women. The days shown, however, do not include the days of actual menstrual periods of these women.

Referring now to the graphs of FIGS. 6 and 7, several days selected respectively from the graphs of FIGS. 4 and 5 are illustrated. In the graphs of FIG. 6 and 7 the measured potential differences are plotted against time, or strictly speaking against the numerical order of successive measurements, for each of the selected days.

It is readily apparent from an examination of these graphs that during the majority of the days of the menstrual cycle, the series of measurements conducted on the same day show potential differences of the same polarity. There is, however, a number of days, usually 2 or 3 within the menstrual cycle, when the series of measurements of the same day reveal a remarkable oscillation of polarity of the measured potential differences. On FIGS. 4 and 6 these days can be identified as August 7, 8 and 9, and on FIGS. 5 and 7 as March 19 and 20.

The days in which the oscillations or fluctuations occur are identified as the days immediately preceding ovulation. This identification was confirmed by independent tests and by results of a study wherein a large number of women were able to avoid or achieve pregnancy by respectively abstaining or engaging in sexual intercourse during the three days following the polarity fluctuations. The nature of the independent tests and the numerical results of the study are further elaborated below.

Referring again to FIGS. 4 and 6, August 7 and 8 are the days in which the subject test woman's body was preparing for ovulation with ovulation occurring within three days of August 8 and probably on August 9th. With reference to FIGS. 5 and 7, the period preparatory for ovulation occurs on March 19 and 20. The actual time of ovulation occurred within three days of March 20th and probably on March 21st.

Additional test results, of the same type as illustrated in FIGS. 4 through 7 are illustrated in Tables 1-5.

TABLE I

| DATE | | VOLTAGE READINGS IN MILIVOLTS | | | |
|---|---|---|---|---|---|
| October | 12 | Menstrual period ends | | | |
| | 13 | −4.2, | −2.1, | −3.4 | |
| | 14 | −3.0, | −2.6, | −2.8 | |
| | 15 | −3.6, | −3.5, | −4.2 | |
| | 16 | −2.8, | −3.6, | −3.5 | |
| | 17 | −1.0, | −1.0, | −2.7 | |
| | 18 | −6.2, | −8.3, | −0.1 | |
| | 19 | −3.2, | −4.7, | −4.1 | |
| | 20 | −4.7, | −2.9, | −2.5 | |
| | 21 | +2.8, | −3.0, | −2.9, | +3.8 |
| | 22 | +5.2, | −5.0, | −4.3, | +6.3 |
| | 23 | −5.1, | −2.4, | −3.5 | |
| | 24 | −4.6, | −2.7, | −1.9 | |
| | 25 | −3.2, | −5.2, | −4.6 | |
| | 26 | −5.5, | −1.7, | −3.2 | |
| | 27 | −4.3, | −4.2, | −0.1 | |
| | 28 | −1.8, | −2.3, | −3.6 | |
| | 29 | −3.4, | −2.4, | −3.6 | |
| | 30 | −1.6, | −1.4, | −2.5 | |
| | 31 | −3.6, | −3.7, | −1.7 | |
| November | 1 | −2.3, | −2.9, | −3.4 | |
| | 2 | −3.5, | −3.7, | −3.6 | |
| | 3 | −4.2, | −2.1, | −3.4 | |
| | 4 | −3.5, | −4.5, | −2.6 | |
| | 5 | −5.3, | −3.3, | −2.0 | |
| | 6 | Menstrual Period Begins | | | |

TABLE II

| DATE | | VOLTAGE READINGS IN MILIVOLTS | | |
|---|---|---|---|---|
| November | 8 | Menstrual Period Ends | | |
| | 9 | −5.8, | −2.6, | −2.4 |
| | 10 | −3.0, | −2.6, | −4.8 |
| | 11 | −1.5, | −2.9, | −4.4 |
| | 12 | −2.8, | −3.6, | −3.5 |
| | 13 | −2.6, | −2.6, | −4.5 |
| | 14 | −2.3, | −2.0, | −3.6 |
| | 15 | −3.4, | −6.0, | −7.4 |

TABLE II-continued

| DATE | VOLTAGE READINGS IN MILIVOLTS | | | |
|---|---|---|---|---|
| 16 | −3.5, | −3.5, | −3.6 | |
| 17 | −4.4, | −4.6, | −3.7 | |
| 18 | +3.0, | −2.0, | +2.2, | +1.6 |
| 19 | +4.2, | −2.8, | +1.9, | +1.9 |
| 20 | −4.3, | −3.6, | −4.9 | |
| 21 | −4.0, | −5.8, | −1.8 | |
| 22 | −1.5, | −2.5, | −3.4 | |
| 23 | −2.9, | −4.9, | −5.3 | |
| 24 | −4.8, | −5.0, | −2.3 | |
| 25 | −2.2, | −5.6, | −4.7 | |
| 26 | −2.0, | −2.8, | −2.6 | |
| 27 | −4.3, | −2.6, | −2.5 | |
| 28 | −1.2, | −1.1, | −2.6 | |
| 29 | −4.0, | −4.5, | −3.9 | |
| 30 | Menstrual Period Begins | | | |

TABLE III

| DATE | VOLTAGE READINGS IN MILIVOLTS | | | |
|---|---|---|---|---|
| November 13 | Menstrual Period Ends | | | |
| 14 | −1.2, | −1.3, | −1.5 | |
| 15 | −1.2, | −1.5, | −2.6 | |
| 16 | −1.4, | −0.4, | −1.4 | |
| 17 | −1.6, | −0.6, | −1.1 | |
| 18 | +2.0, | −1.3, | +1.6 | |
| 19 | +1.8, | +1.1, | −1.2 | |
| 20 | −7.1, | −7.3, | −7.0, | −7.7 |
| 21 | −3.1, | −3.0, | −3.3 | |
| 22 | −1.1, | −1.7, | −1.9 | |
| 23 | −1.4, | −1.6, | −1.7 | |
| 24 | −1.5, | −1.6, | −0.2 | |
| 25 | −1.8, | −2.0, | −1.1 | |
| 26 | −1.0, | −1.6, | −0.9 | |
| 27 | −2.7, | −2.0, | −2.5 | |
| 28 | −2.9, | −2.7, | −2.6 | |
| 29 | −2.1, | −2.0, | −1.9 | |
| 30 | −5.4, | −3.6, | −4.2 | |
| December 1 | −1.2, | −1.6, | −1.2 | |
| 2 | −1.9, | −2.2, | −0.6 | |
| 3 | −0.9, | −0.9, | −1.8, | −2.6 |
| 4 | −3.4, | −5.1, | −6.8, | −4.8 |
| 5 | −3.5, | −6.8, | −2.3, | −2.9 |
| 6 | Menstrual Period Begins | | | |

TABLE IV

| DATE | VOLTAGE READINGS IN MILIVOLTS | | | | |
|---|---|---|---|---|---|
| October 31 | Menstrual Period Ends | | | | |
| November 1 | −3.2, | −8.1, | −8.3, | −4.6, | −2.8 |
| 2 | −8.3, | −4.6, | −7.8, | −4.1, | −7.8 |
| 3 | −3.6, | −8.1, | −4.1, | −5.6, | −7.8 |
| 4 | −3.2, | −8.3, | −4.6, | −4.1, | −7.8 |
| 5 | −9.1, | −7.3, | −4.1, | −2.3, | −4.1 |
| 6 | No reading | | | | |
| 7 | −7.3, | −4.1, | −9.2, | −7.8, | −3.1 |
| 8 | −6.9, | −8.1, | −7.3, | −4.1, | −9.1 |
| 9 | −2.8, | −5.3, | −4.9, | −8.1, | −9.1 |
| 10 | −3.6, | −8.1, | −7.3, | −4.6, | −7.3 |
| 11 | −9.3, | −4.7, | −8.3, | −4.1, | −8.2 |
| 12 | −8.3, | −4.1, | −5.6, | −7.8, | −4.1 |
| 13 | −3.1, | −8.2, | −8.3, | −4.1, | −4.2 |
| 14 | +8.3, | −4.6, | −9.3, | +4.1, | +8.1 |
| 15 | +9.3, | +4.6, | +7.3, | −4.1, | −9.2 |
| 16 | +6.3, | −4.1, | −9.3, | −7.1, | +3.2 |
| 17 | −8.1, | −9.3, | −4.5, | −9.5, | −4.4 |
| 18 | −4.9, | −3.2, | −4.5, | −6.8, | −4.9 |
| 19 | No reading | | | | |
| 20 | −8.3, | −4.1, | −8.3, | −4.7, | −8.3 |
| 21 | −7.8, | −3.2, | −8.1, | −9.2, | −7.8 |
| 22 | −4.1, | −3.1, | −4.7, | −8.3, | −4.1 |
| 23 | −9.2, | −8.3, | −4.5, | −6.8, | −4.4 |
| 24 | −8.1, | −3.2, | −4.1, | −5.1, | −6.2 |
| 25 | Menstrual Period Begins | | | | |

TABLE V

| DATE | VOLTAGE READINGS IN MILIVOLTS | | | | |
|---|---|---|---|---|---|
| October 27 | Menstrual Period Ends | | | | |
| 28 | −8.3, | −4.1, | −5.6, | −3.8, | −4.1 |
| 29 | −8.9, | −4.1, | −6.3, | −4.9, | −3.1 |
| 30 | −8.1, | −9.2, | −7.8, | −3.7, | −8.4 |
| 31 | −5.6, | −8.3, | −4.1, | −5.6, | −5.3 |
| November 1 | −4.7, | −8.3, | −4.5, | −6.8, | −3.1 |
| 2 | −8.2, | −4.9, | −7.8, | −3.2, | −4.1 |
| 3 | −6.3, | −4.7, | −8.3, | −5.6, | −7.8 |
| 4 | −3.6, | −8.3, | −4.9, | −9.8, | −3.2 |
| 5 | −7.8, | −3.2, | −8.9, | −7.8, | −9.3 |
| 6 | −3.9, | −9.8, | −7.8, | −3.2, | −6.8 |
| 7 | −3.7, | −8.3, | −5.6, | −7.8, | −3.2 |
| 8 | −9.3, | −9.8, | −8.3, | −5.6, | −9.4 |
| 9 | +6.3, | +4.9, | −3.1, | −4.9, | +7.8 |
| 10 | +4.9, | −6.8, | −3.7, | +9.4, | +7.4 |
| 11 | +7.3, | −4.6, | −9.1, | −4.6, | −9.9 |
| 12 | −6.3, | −4.7, | −8.3, | −4.9, | −3.1 |
| 13 | −9.8, | −3.6, | −4.4, | −5.6, | −2.3 |
| 14 | −8.2, | −6.8, | −4.6, | −8.3, | −5.6 |
| 15 | −6.3, | −4.7, | −8.2, | −5.6, | −7.8 |
| 16 | −9.3, | −4.7, | −8.4, | −5.6, | −8.3 |
| 17 | −9.2, | −8.3, | −4.6, | −8.3, | −4.3 |
| 18 | −3.6, | −7.8, | −4.7, | −8.3, | −9.1 |
| 19 | −5.6, | −5.8, | −4.1, | −3.9, | −9.1 |
| 20 | Menstrual Period Begins | | | | |

Each of the above tables represents the results of daily successive measurements of potential differences taken on the days occurring between two menstrual periods of a subject test woman. The results and conclusions obtained from these tables are the same as the ones obtained from an examination of the graphs of FIGS. 4–7. Namely, in each case the time of ovulation is preceded by a conspicuous oscillation or fluctuation of the measured potential differences of the same day.

It is to be noted that the test results given on the charts of FIGS. 4–7 and in Tables 1–5 are to be construed as illustrative examples only. A significantly larger number of tests yielding like results were obtained.

A utilitarian application of the herein described process of identifying a phase of ovulation within the menstrual cycle of a woman is readily apparent. By monitoring the potential differences between her two hands, preferrably the index fingers, in the manner described above, a woman is able to identify a time period in which sexual intercourse most probably would result in pregnancy. Accordingly, depending on whether she wishes to become pregnant or avoid pregnancy she can engage or abstain from sexual intercourse.

In a study, briefly referred to above, a total of 1432 menstrual cycles of 580 women were monitored according to the above described process of the present invention. Verification of ovulation as predicted from the test results, was sought and obtained by endometrial biopsy in 51 menstrual cycles, and in another 65 menstrual cycles by monitoring the basal body temperature.

The women involved were broadly in the 14–52 age group, with 344 women in the 19–29 years age group, and 244 in the 30–45 years age group.

One hundred and twenty one women out of the total of 580 had been desirous of becoming pregnant for a substantial time prior to these tests, some up to 8 years. As a result of applying the herein described method for identifying the ovulatory phase, 105 women out of the 121 were able to become pregnant.

Four hundred thirty four women in the study representing a total of 1150 menstrual cycles wished to avoid pregnancy by the use of this method, and were able to do so. There was a control group of 13 women who were taking steroidal birth control pills, and therefore could not have had an ovulatory phase in their menstrual cycles. The method of the present invention, accordingly, failed to identify an ovulatory phase in these women.

It is to be emphasized that the herein described method has a high degree of accuracy. Nevertheless as all methods and processes dealing with biological systems, it is subject to certain inexactitudes and limitations which are inherent in the biological sciences. Certain ailments and such extraneous factors as certain medications may particularly detract from the accuracy of this method.

What has been described above is a reliable system of measuring true potential differences between two points of the female body and thereby identifying an ovulatory phase within the menstrual cycle of the female. It will be apparent to those skilled in the art that various modifications of the present invention are possible, and accordingly the scope of the present invention should be interpreted solely from the following claims.

What is claimed is:

1. A process for monitoring the state of a menstrual cycle of a woman comprising the steps of:
    measuring at least the polarity of a direct current potential between at least two spaced apart portions of the woman's body, said spaced apart portions being located respectively on the right and left side of the woman's body, the step of measuring including applying a pair of suitable electrodes to said portions of the woman's body, observing a readout of said potential on a display and successively repeating said applying and observing steps at least three times;
    repeating said measuring step every day throughout at least a substantial portion of the days of the woman's menstrual cycle, and
    identifying from said measurements a phase of ovulation within the woman's menstrual cycle.

2. The process of claim 1 wherein the observing step includes a step of waiting for a substantially stable value of the potential, said stable value being considered as the read-out.

3. The process of claim 2 wherein the time period elapsed between an applying and an observing step and a subsequent applying and observing step is less than 5 minutes.

4. The process of claim 3 including the additional step of recording each observed value of the potential.

5. The process of claim 4 wherein the spaced apart portions of the woman's body each comprise a portion of the outer skin surface of each hand of the woman.

6. The process of claim 5 wherein the spaced apart portions each comprise one of the fingers of each hand of the woman.

7. A process for monitoring a menstrual cycle of a human female for identifying an ovulation phase within the cycle, the process comprising the steps of:
    measuring with a suitable voltage meter at least the polarity of a true direct current potential between two spaced apart points of the outer surface of the female's body, the spaced apart points being located respectively on the right and left hand side of the woman's body, said measuring being performed on substantially every day throughout at least a substantial portion of the menstrual cycle and comprising the steps of repeatedly and within short time intervals observing at least the polarity reading of the voltage meter;
    selecting each of those days of the menstrual cycle wherein the repeated polarity readings include at least two readings of opposite polarity, and
    identifying the selected days of the menstrual cycle as days immediately preceding a probable time of ovulation.

8. The process of claim 7 wherein the spaced apart portions of the female's body comprise two hands of the female.

9. The process of claim 8 wherein the spaced apart portions comprise a finger of each hand.

10. The process of claim 7 wherein the steps of repeatedly observing at least a polarity reading are completed in less than 30 minutes.

11. The process of claim 10 wherein the observing step is performed at least three times.

12. The process of claim 7 wherein the voltage meter also supplies a numerical value of the potential and said numerical value is observed.

13. The process of claim 7 wherein the measuring step further includes the steps of repeatedly and within short time intervals applying suitable electrodes to the spaced apart points and wherein each step of observing is performed after a step of applying.

14. The process of claim 13 wherein the voltage meter also supplies a numerical value of the potential, and wherein the measuring step further includes after each step of applying the electrodes a step of waiting until a numerical value of the potential is substantially stable, said substantially stable numerical value being observed in the observing step.

15. In a process for monitoring the menstrual cycle of a human female including the steps of applying a pair of suitable electrodes connected to a suitable voltage meter to two spaced apart portions of the body of the female, the two spaced apart portions being located respectively on the right and left side of the female's body, measuring at least the polarity of a true direct current potential between the two portions, repeating the applying and measuring steps for at least a substantial portion of the days of the menstrual cycle of the female and identifying from the measurements a probable ovulation phase of the menstrual cycle, the improvement comprising:
    successively performing the applying step and measuring steps several times on each day;
    selecting those days wherein the measuring steps resulted in at least two readings having opposite polarity, and
    designating in the identifying step said selected days as days immediately preceding a probable time of ovulation of the female.

16. The improvement of claim 15 wherein a time period elapsing between an applying and measuring step and a subsequent applying and measuring step is less than five minutes.

17. The improvement of claim 16 wherein the spaced apart portions of the body of the female comprise a finger of each hand.

* * * * *

UNITED STATES PATENT AND TRADEMARK OFFICE
CERTIFICATE OF CORRECTION

PATENT NO. : 4,246,907
DATED : January 27, 1981
INVENTOR(S) : Russel F. Bullock

It is certified that error appears in the above—identified patent and that said Letters Patent is hereby corrected as shown below:

Column 6, line 45, delete "-4.3," and insert --+4.3,--.

Signed and Sealed this

Nineteenth Day of May 1981

[SEAL]

*Attest:*

RENE D. TEGTMEYER

*Attesting Officer*     *Acting Commissioner of Patents and Trademarks*